(12) United States Patent
Denoziere et al.

(10) Patent No.: US 8,475,503 B2
(45) Date of Patent: Jul. 2, 2013

(54) METHODS FOR FORMING IMPLANTS WITH SELECTIVELY EXPOSED MESH FOR FIXATION AND RELATED IMPLANTS

(75) Inventors: Guilhem Denoziere, Atlanta, GA (US); Daniel Tomko, Lawrenceville, GA (US); Anish Ghodadra, Lilburn, GA (US)

(73) Assignee: MiMedx Group, Inc., Kennesaw, GA (US)

( * ) Notice: Subject to any disclaimer, the term of this patent is extended or adjusted under 35 U.S.C. 154(b) by 206 days.

(21) Appl. No.: 12/977,336

(22) Filed: Dec. 23, 2010

(65) Prior Publication Data

US 2011/0089599 A1    Apr. 21, 2011

Related U.S. Application Data

(62) Division of application No. 12/016,223, filed on Jan. 18, 2008, now Pat. No. 7,879,100.

(60) Provisional application No. 60/885,682, filed on Jan. 19, 2007.

(51) Int. Cl.
*A61B 17/88* (2006.01)

(52) U.S. Cl.
USPC ............... 606/279; 623/17.11; 623/17.16

(58) Field of Classification Search
USPC ..... 606/246, 248, 249, 279; 623/17.11–17.16
See application file for complete search history.

(56) References Cited

U.S. PATENT DOCUMENTS

| | | | |
|---|---|---|---|
| 4,759,766 A | 7/1988 | Buettner-Janz et al. | |
| 5,314,477 A | 5/1994 | Marnay | |
| 5,401,269 A | 3/1995 | Buttner-Janz et al. | |
| 5,458,643 A | 10/1995 | Oka et al. | |
| 5,556,431 A | 9/1996 | Buttner-Janz | |
| 5,981,826 A | 11/1999 | Ku et al. | |
| 6,231,605 B1 | 5/2001 | Ku | |
| 6,629,997 B2 | 10/2003 | Mansmann | |
| 2002/0026244 A1 | 2/2002 | Trieu | |
| 2002/0077701 A1 | 6/2002 | Kuslich | |
| 2005/0055099 A1 | 3/2005 | Ku | |
| 2006/0265075 A1 | 11/2006 | Baumgartner et al. | |
| 2007/0093912 A1* | 4/2007 | Borden .................. | 623/23.75 |
| 2007/0179621 A1 | 8/2007 | McClellan et al. | |

FOREIGN PATENT DOCUMENTS

| | | |
|---|---|---|
| EP | 0107055 | 5/1984 |
| EP | 0505634 | 9/1992 |
| WO | WO 2007/087366 | 8/2007 |

OTHER PUBLICATIONS

Stauffer et al., Peppas, Poly (vinyl alcohol) hydrogels prepared by freezing-thawing cyclic processing, Polymer, 1992, pp. 3932-3936, v. 33.

* cited by examiner

*Primary Examiner* — Eduardo C Robert
*Assistant Examiner* — Christina Negrellirodriguez
(74) *Attorney, Agent, or Firm* — Myers Bigel Sibley & Sajovec, P.A.

(57) ABSTRACT

Methods for forming molded orthopedic implants with at least one mesh substrate having opposing upper and lower primary surfaces. At least a major portion of the mesh substrate lower primary surface is integrally moldably attached to the molded implant body. The methods are carried out so that the mesh substrate has at least one selectively exposed region devoid of molded material that exposes at least a portion of the mesh substrate upper surface to at least a partial thickness of the mesh substrate so as to allow for tissue in-growth in the at least one exposed region of the mesh substrate.

19 Claims, 11 Drawing Sheets

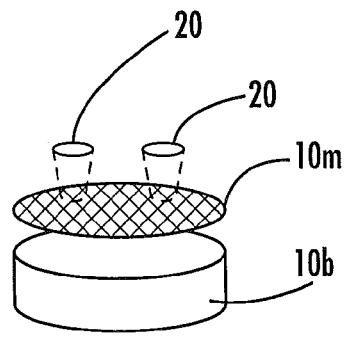
FIG. 4A
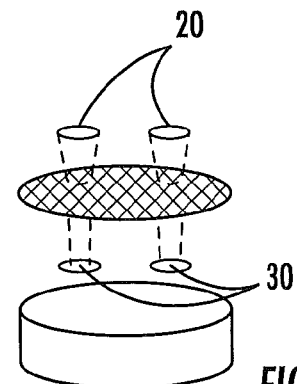
FIG. 5
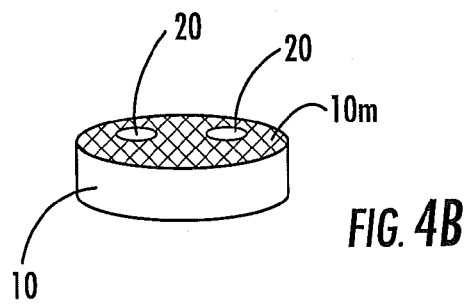
FIG. 4B
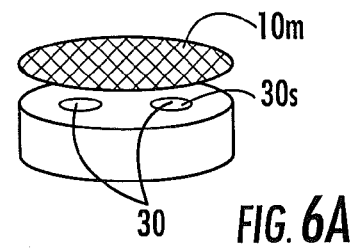
FIG. 6A
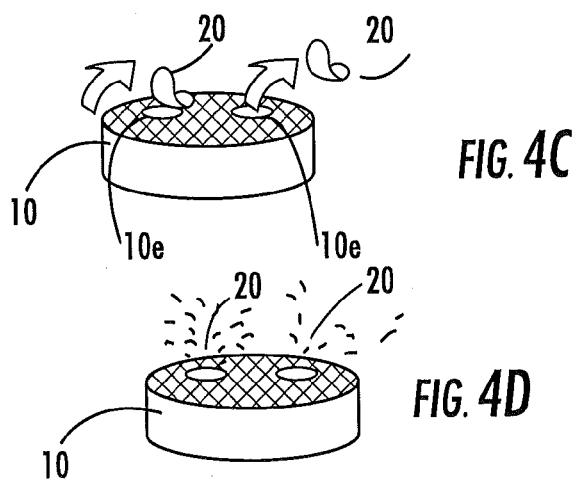
FIG. 4C
FIG. 4D
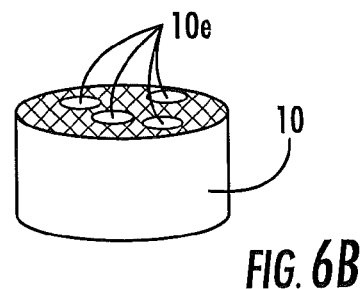
FIG. 6B
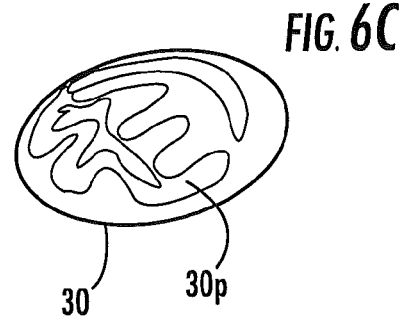
FIG. 6C

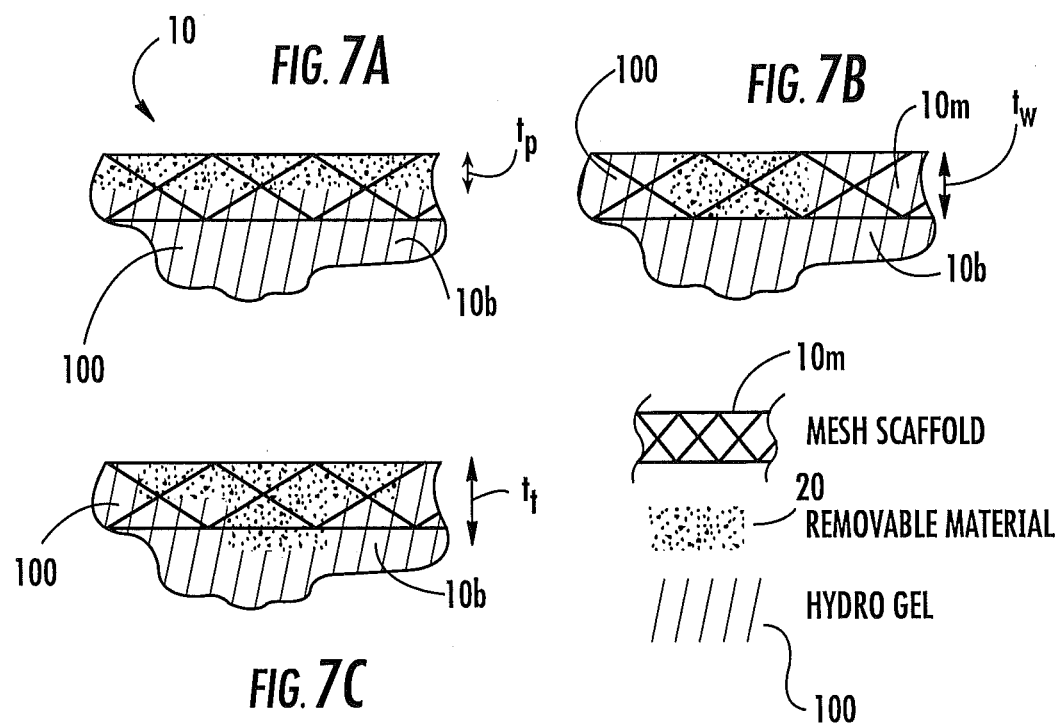

METHODS FOR FORMING IMPLANTS WITH SELECTIVELY EXPOSED MESH FOR FIXATION AND RELATED IMPLANTS

RELATED APPLICATIONS

This application is divisional of U.S. patent application Ser. No. 12/016,223, filed Jan. 18, 2008 now U.S. Pat. No. 7,879,100, which claims the benefit of priority of U.S. Provisional Patent Ser. No. 60/885,682, filed Jan. 19, 2007, the contents of which are hereby incorporated by reference as if recited in full herein.

FIELD OF THE INVENTION

The invention relates to implantable orthopaedic devices and may be particularly relevant for spinal total disc replacement (TDR) implants.

BACKGROUND OF THE INVENTION

The vertebrate spine is made of bony structures called vertebral bodies that are separated by relatively soft tissue structures called intervertebral discs. The intervertebral disc is commonly referred to as a spinal disc. The spinal disc primarily serves as a mechanical cushion between the vertebral bones, permitting controlled motions between vertebral segments of the axial skeleton. The disc acts as a joint and allows physiologic degrees of flexion, extension, lateral bending, and axial rotation. To operate normally, the disc should have sufficient flexibility to allow these motions and have sufficient mechanical properties to resist the external forces and torsional moments caused by the vertebral bones.

The normal disc is a mixed avascular structure having two vertebral end plates ("end plates"), an annulus fibrosis ("annulus") and a nucleus pulposus ("nucleus"). Typically, about 30-50% of the cross sectional area of the disc corresponds to the nucleus. Generally described, the end plates are composed of thin cartilage overlying a thin layer of hard, cortical bone that attaches to the spongy cancellous bone of the vertebral body. The end plates act to attach adjacent vertebrae to the disc. Together, the annulus and nucleus support the spine by flexing with forces produced by the adjacent vertebral bodies during bending, lifting, etc.

There are several types of treatment currently being used for treating herniated or degenerated discs: conservative care, discectomy, nucleus replacement, fusion and prosthesis total disc replacement (TDR). It is believed that many patients with lower back pain will get better with conservative treatment of bed rest. For others, more aggressive treatments may be desirable.

Discectomy can provide good short-term results. However, a discectomy is typically not desirable from a long-term biomechanical point of view. Whenever the disc is herniated or removed by surgery, the disc space will narrow and may lose much of its normal stability. The disc height loss may cause osteo-arthritis changes in the facet joints and/or compression of nerve roots over time. The normal flexibility of the joint is lost, creating higher stresses in adjacent discs. At times, it may be necessary to restore normal disc height after the damaged disc has collapsed.

Fusion is a treatment by which two vertebral bodies are fixed to each other by a scaffold. The scaffold may be a rigid piece of metal, often including screws and plates, or allo or auto grafts. Current treatment is to maintain disc space by placement of rigid metal devices and bone chips that fuse two vertebral bodies. The devices are similar to mending plates with screws to fix one vertebral body to another one. Alternatively, hollow metal cylinders filled with bone chips can be placed in the intervertebral space to fuse the vertebral bodies together (e.g., LT-Cage™ from Sofamor-Danek or Lumbar I/F CAGE™ from DePuy). These devices have disadvantages to the patient in that the bones are fused into a rigid mass with limited, if any, flexible motion or shock absorption that would normally occur with a natural spinal disc. Fusion may generally eliminate symptoms of pain and stabilize the joint. However, because the fused segment is fixed, the range of motion and forces on the adjoining vertebral discs can be increased, possibly enhancing their degenerative processes.

Some recent TDR devices have attempted to allow for motion between the vertebral bodies through articulating implants that allow some relative slippage between parts (e.g., ProDisc®, Charite™), see, for example, U.S. Pat. Nos. 5,314,477; 4,759,766; 5,401,269 and 5,556,431. As an alternative to the metallic-plate, multi-component TDR designs, a flexible solid elastomeric spinal disc implant that is configured to simulate natural disc action (i.e., can provide shock absorption and elastic tensile and compressive deformation) is described in U.S. Patent Application Publication No. 2005/0055099 to Ku, the contents of which are hereby incorporated by reference as if recited in full herein.

Notwithstanding the above, there remains a need to provide alternative fixation structures that can help affix orthopaedic implants to local tissue or bone while also allowing for substantially normal disc action.

SUMMARY OF EMBODIMENTS OF THE INVENTION

Embodiments of the invention are directed to orthopaedic implants with selectively exposed mesh adapted for double integration fixation.

Molded orthopaedic implants include at least one mesh substrate having opposing upper and lower primary surfaces. At least a major portion of the mesh substrate lower primary surface is integrally moldably attached to the molded implant body. The mesh substrate has at least one selectively exposed region devoid of molded material that exposes at least a portion of the mesh substrate upper surface to at least a partial thickness of the mesh substrate so as to allow for tissue in-growth in the at least one exposed region of the mesh substrate.

The at least one exposed region can be a region that extends over at least a major portion of the upper surface of the mesh substrate and that extends into a partial thickness of the mesh substrate. The at least one exposed region may have a gradient configuration whereby increasing amounts of molded material reside closer to the lower primary surface.

The at least one exposed region can be a plurality of discrete spaced apart exposed regions that extend through the upper primary surface and extend a partial thickness into or wholly through the mesh substrate. In particular embodiments, some of the regions can be between about 5-10 mm in cross-sectional width.

In some embodiments, the implant can include an intermediate material layer residing between the lower primary surface of the mesh substrate and an upper portion of the molded body whereby the intermediate material layer resides proximate to the at least one exposed mesh substrate region. The intermediate layer may be porous or non-porous (substantially impermeable) and may be formed of a single sheet of material or several discrete pieces.

Other embodiments are directed to methods of fabricating an implantable prosthesis. The methods include: (a) placing an inferior mesh layer on a floor of a three-dimensional mold; (b) introducing moldable material into the mold; (c) placing a superior mesh layer on a top surface of the moldable material in the mold; (d) heating the mold with the moldable material to a desired temperature so that the mold is heated; then (e) forming a molded implant body formed by the heated moldable material whereby the mesh layers are integrally moldably attached to the molded body formed by the moldable material; and (f) selectively exposing at least one of the inferior and superior mesh layers so that at least one region is substantially devoid of the moldable material whereby the exposed region promotes tissue in-growth therein.

In some embodiments, the selectively exposing step includes placing a temporary mesh layer over at least a portion of at least one of an upper primary surface of the superior layer or a lower primary surface of the inferior mesh layer, then after the forming step, removing the temporary mesh layer to selectively expose the mesh of the superior and/or inferior mesh layers while at least a major portion of the mesh layers are integrally molded to the molded implant body.

In some embodiments, the selectively exposing step comprises placing calcium salt on selective regions of the inferior and superior mesh layers before the forming step.

In some embodiments, the selectively exposing step includes placing a temporary silicone layer over at least a portion of at least one of an upper primary surface of the superior layer or a lower primary surface of the inferior mesh layer to inhibit moldable material from entering at least a top portion of the superior mesh layer or a bottom portion of the inferior mesh layer, respectively, during the forming step, then after the forming step, removing the temporary silicone layer to selectively expose the mesh of the superior and/or inferior mesh layers.

In some embodiments, the selectively exposing step includes placing intermediate mesh segment layers having smaller areas than the inferior and superior mesh layers, between at least one of the superior layer or the inferior mesh layer and the moldable material to locally inhibit moldable material from entering selected regions of the superior mesh layer and the inferior mesh layer, respectively.

In some embodiments, the selectively exposing step includes placing an intermediate substantially impermeable layer between at least one of the superior layer or the inferior mesh layer and the moldable material to locally inhibit moldable material from entering selected regions of the superior mesh layer or the inferior mesh layer, respectively, during the forming step.

In some embodiments, the selectively exposing step includes inhibiting the moldable material from extending through localized regions of an upper portion of the superior mesh layer and a lower portion of the inferior mesh layer during the forming step.

In some embodiments, the selectively exposing step includes allowing the moldable material to enter the mesh superior and inferior layers while inhibiting the moldable material from extending through at least a major portion of an area of an upper portion of the superior mesh layer and a lower portion of the inferior mesh layer during the forming step.

In some embodiments, the selectively exposing step includes flowing PVA hydrogel moldable material into the inferior and superior mesh layers during the forming step whereby a density gradient of the hydrogel moldable material extends in the mesh substrate whereby a lesser density of moldable material resides on an outermost bounds of the implant body.

In some embodiments, the selectively exposing step comprises placing a temporary mesh layer comprising a resorbable material (e.g., any suitable biocompatible salt) over at least a portion of at least one of an upper primary surface of the superior layer or a lower primary surface of the inferior mesh layer, then after the forming step, removing the temporary mesh layer to selectively expose the mesh of the superior and/or inferior mesh layers.

In some embodiments, the selectively exposing step comprises directing liquid, which may be pressurized to higher or lower pressures or even unpressurized (just flowing), to remove molded material residing in a target, localized region of at least one of the superior and inferior mesh layers.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 4A is a schematic, exploded illustration of an implant with a mesh layer and a molded implant body according to embodiments of the invention.

FIG. 4B is a schematic illustration of the implant shown in FIG. 4A with the mesh substrate moldably attached thereto according to embodiments of the invention.

FIG. 4C is a schematic illustration of removable temporary layer(s) of material attached to the molded implant according to embodiments of the present invention.

FIG. 4D is a schematic illustration of the implant shown in FIG. 4A having a naturally resorbable material according to embodiments of the present invention.

FIG. 5 is a schematic illustration of a different configuration of a mesh layer with cooperating selective exposure material according to embodiments of the invention.

FIG. 6A illustrates an exploded view of an implant with the mesh layer and insert supplemental material used to form locally exposed regions according to embodiments of the present invention.

FIG. 6B is a schematic illustration of the device shown in FIG. 6A with the locally exposed mesh regions provided at demolding based on the insert material according to embodiments of the present invention.

FIG. 6C is a top view of an alternate insert configuration that may be used in lieu of the insert shown in FIG. 6A according to embodiments of the present invention.

FIGS. 7A-7C are schematic illustrations of different configurations of an implant with a mesh scaffold having removable material used to form at least one exposed region (substantially devoid of hydrogel or other moldable material) in the mesh layer according to embodiments of the invention.

DETAILED DESCRIPTION

Figure 1A:
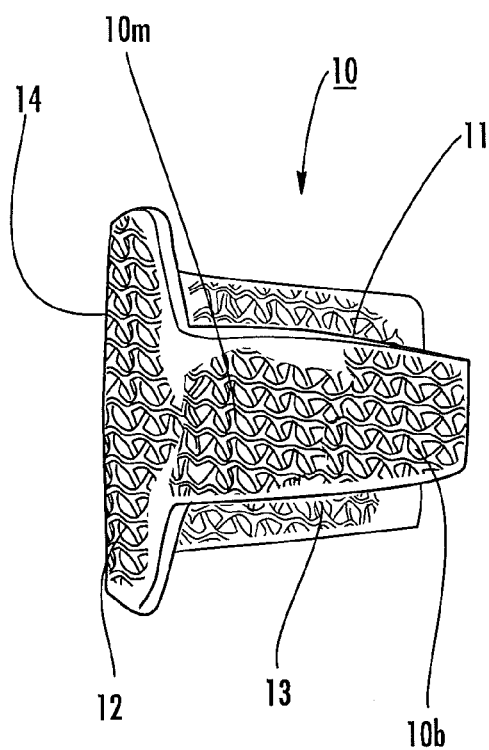
FIG. 1A is a side perspective view of a spinal disc implant according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "spinal disc implant" and "spinal disc prosthesis" are used interchangeably herein to designate total disc replacements using an implantable total spinal disc replacement prosthesis (rather than a nucleus only) and as such are configured to replace the natural spinal disc of a mammalian subject (for veterinary or medical (human) applications). In contrast, the term "spinal implant" refers to both TDR spinal disc implants and alternative spinal implants, such as, for example, a spinal annulus or a spinal nucleus implant.

The term "flexible" means that the member can be flexed or bent. In some embodiments, the keel is flexible but has sufficient rigidity to be substantially self-supporting so as to be able to substantially maintain a desired configuration outside of the body. The keel can include reinforcing materials and/or structure to increase its rigidity.

The term "keel" means an implant component, feature or member that is configured to be received in a recess or mortise in an adjacent bone to facilitate short and/or long-term fixation and/or to provide twist or torsion resistance in situ. The term "keel" also includes a discontinuous keel configuration and/or a keel configuration that does not extend the entire length of the implant body, such as one or more axially aligned or offset keels.

The team "mesh" means any material in any form including, for example, knotted, braided, extruded, stamped, knitted, woven or otherwise, and may include a material with a substantially regular foramination pattern and/or an irregular foramination pattern.

The term "macropores" refers to apertures having at least about a 0.5 mm diameter or width size, typically a diameter or width that is between about 1 mm to about 3 mm, and more typically a diameter or width that is between about 1 mm to about 1.5 mm (the width dimension referring to non-circular apertures). Where mesh keels are used, the macropores are typically larger than the openings or foramina of the mesh substrate. The macropores may promote bony through-growth for increased fixation and/or stabilization over time.

The term "loop" refers to a shape in the affected material that has a closed or nearly closed turn or configuration/shape. For example, the loop can have its uppermost portion merge into two contacting lower portions or into two proximately spaced apart lower portions. The term "fold" means to bend over and the bend of the fold may have a sharp or rounded edge. The terms "pleat" or "fold" refer to doubling material on itself (with or without sharp edges).

The term "local" and derivatives thereof refers to target sub-portions of the device rather than a global feature. The term "orthopaedic" refers to medical implants or devices used to treat disorders of the skeletal system and related motor organs.

The term "film" refers to a thin material, typically between about 0.001 mm to about 0.5 mm thick, and may be porous or non-porous (e.g., substantially or totally impermeable).

Figure 1B:
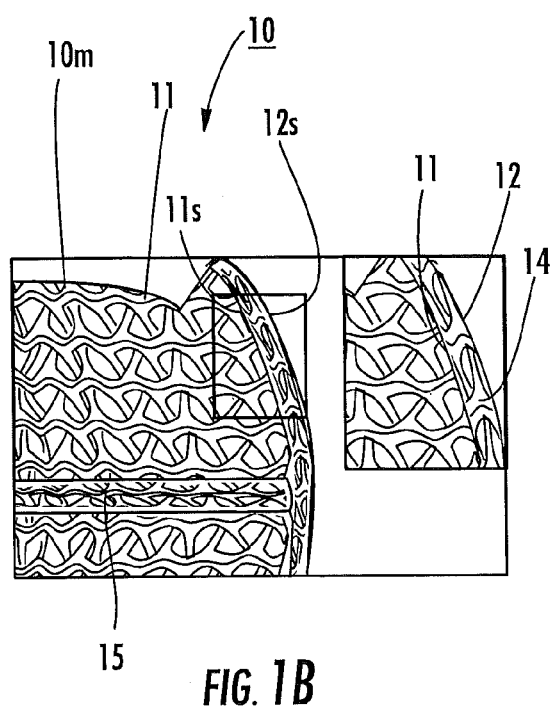
FIG. 1B is a top view of a portion of the implant shown in FIG. 1A with an enlarged view of one region thereof.

As shown in FIGS. 1A and 1B, an implant 10 can include at least one porous mesh material layer 10m, shown as including three discrete layers 11, 12, 13 that can be moldably attached to a primary molded body 10b. In the embodiment shown, the mesh layers 10m include superior and inferior primary surface mesh-covering layers 11, 13, respectively and an annulus surface mesh-covering layer 12. The annulus layer 12 can be formed as a continuous or seamed ring to radial and/or axial expansion of the body 10b. In other embodiments, the annulus cover layer 12 can be discontinuous about the molded primary body 10b.

Figure 3:
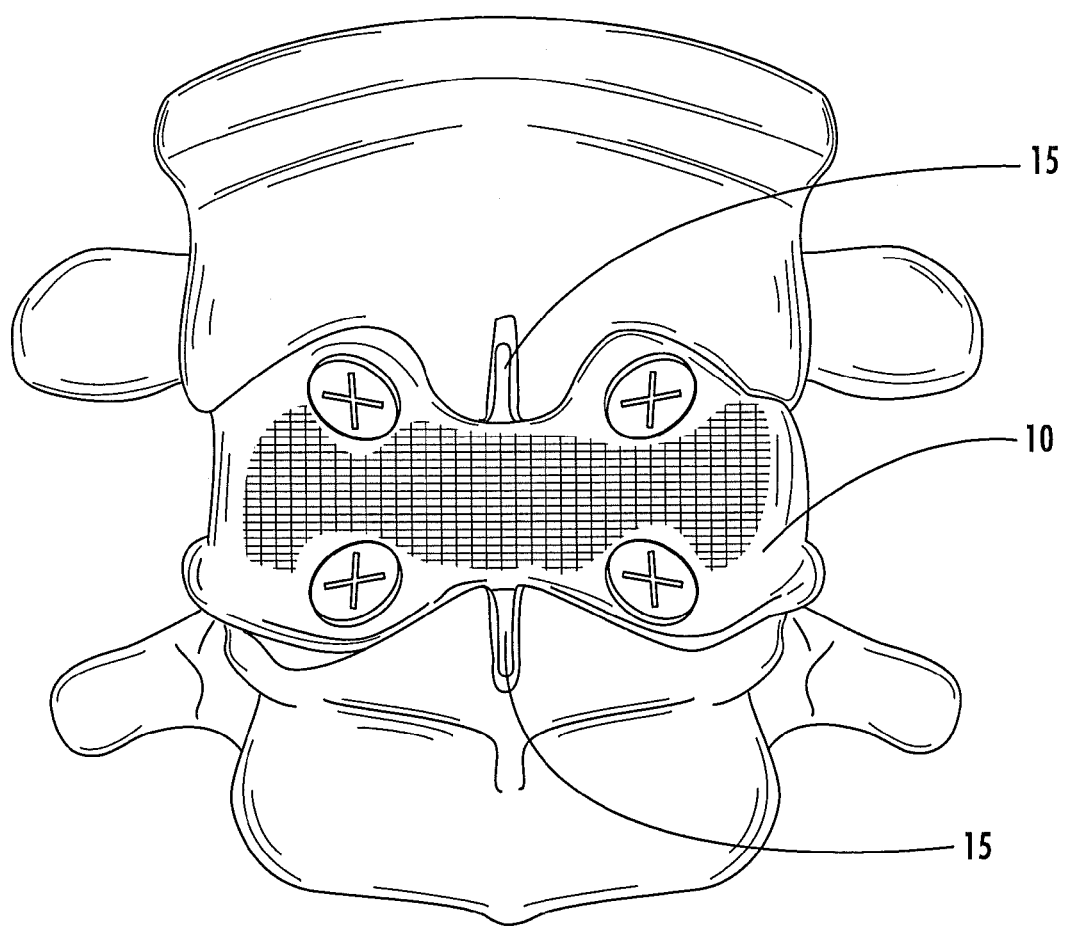
FIG. 3 is a front view of an implant similar to that shown in FIG. 1A in position according to embodiments of the invention.

As shown, the implant 10 may also include at least one flexible keel 15 on each of the end plate surfaces formed by the mesh material 11, 13. FIG. 3 illustrates that the keel 15 can reside in a mortise in adjacent bone when implanted. One or more pre-molding apertures and/or post-molding apertures (macropores) may be formed in the keel 15 and/or skirt 14 for vertebral bone attachment. If a cutting process is used, the cutting process (e.g., ultrasonic cutting, laser cutting, thermal cutting, RF cutting or other suitable techniques) may locally melt the two layers of mesh or keel pieces together, creating at that point a fused direct connection between the two layers.

FIG. 3 also illustrates a different shape of the skirt 14. Although the implant 10 is shown as a spinal (TDR) disc shape and is primarily described with respect to this embodiment for clarity of discussion, the implant 10 can have other shapes according to a desired function and target repair site, and is not limited to spinal disc implants.

The molded body 10b can be of any suitable biocompatible material appropriate to the target repair site, typically an elastomeric material, such as polymer, co-polymer or derivatives or combinations thereof. In particular embodiments, the implant 10 can be a TDR implant that has a solid unitary body 10b of molded crystalline hydrogel of polyvinyl alcohol (PVA) known as Salubria® from SaluMedica, Inc., located in Atlanta Ga.

Similarly, the mesh 10m can be of any suitable biocompatible material. Where mesh layers 10m are used on more than one surface, the different mesh layers may be of different mesh material, thickness and/or mesh porosity. As shown, in FIGS. 1A and 1B, the endplate mesh layers 11, 13 may have a different mesh pattern than the mesh ring 12, with the peripheral mesh ring 12 having smaller pore sizes from that of the endplate mesh layers 11, 13. The pore dimensions of the superior/inferior (e.g., endplate) mesh layers 11, 13 can be selected to promote tissue in-growth. Exemplary pore sizes for tissue ingrowth and/or bone ingrowth into the exposed mesh scaffold of the endplate mesh layers 11, 13 is typically between about 0.5 mm to about 1 mm. Smaller pore sizes may be used on the annular mesh layer 12, typically between about 0.1 mm to about 0.5 mm as this mesh 12 may not be exposed (e.g., is substantially encapsulated in the mold material) and has a desired strength related to mesh density. The mesh layers 11, 13 can be any suitable thickness and pore pattern configured to promote tissue in-growth, and may typically be between about 0.5 mm to about 5 mm thick, more typically between about 0.7 mm to about 2 mm thick, such as about 0.75 mm thick.

In some embodiments, the mesh layers 10m can all be polyester mesh layers that may be extruded, knitted, braided, woven or otherwise formed into a mesh pattern. In some embodiments, the mesh comprises a multi-filament fiber(s) that can provide increased strength over conventional polyester material. For example, the mesh 10m can comprise yarns of a polyester mesh multifilament fiber that, for example, can be made out of a High Tenacity Polyester Teraphthalate (HTPET), which typically has a longer molecular chain than conventional polyester material, therefore providing more strength to the mesh than a regular polyester material. In some embodiments, the mesh can be a high strength mesh that using a ball burst test (ref. ASTM D3787-01), can have a burst value between about 1500-3000N and also a slope of the linear portion of the load/displacement curve of between about 150-300 N/mm. In particular embodiments, one or more of the mesh layers 11, 12, 13 can include a high strength polyester mesh of about 0.7 mm thick that is similar to or the same as that available as Fablok Mills Mesh #9464 from Fablok Mills, Inc., located in Murray Hill, N.J.

As shown in FIGS. 1A, 1B, 2A, and 2B, the TDR implant 10 includes three separate pieces of mesh covering material 11, 12, 13 that are each integrally molded to attach to the primary body 10b of the implant; one to the upper primary surface; one to the lower primary surface; and one as a peripheral ring around the outer upwardly extending surface. The upper and lower primary surfaces are also known as endplate surfaces. As shown in FIG. 1B, the edges of the three pieces of mesh are not required to attach together but can be each integrally molded to the implant body, embedded, at least partially, in the moldable (e.g., PVA) material. One purpose of the endplate mesh 11, 13 can be to promote tissue in-growth. The peripheral mesh ring 12 can embed in the molded (e.g., PVA) material so as to increase radial strength of the implant to limit radial expansion under load, but the mesh ring 12 may be sufficiently covered and/or embedded in the molded body so as to inhibit tissue in-growth therein.

Figure 2A:
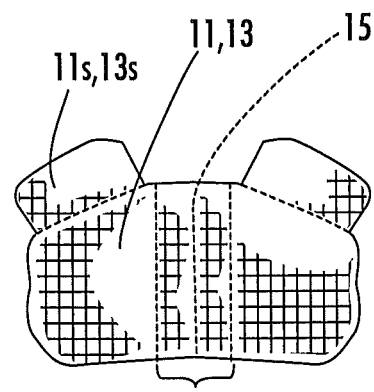
FIG. 2A is a top view of a superior/inferior mesh layer that can be used to form the implant shown in FIG. 1A according to embodiments of the invention.
Figure 2B:
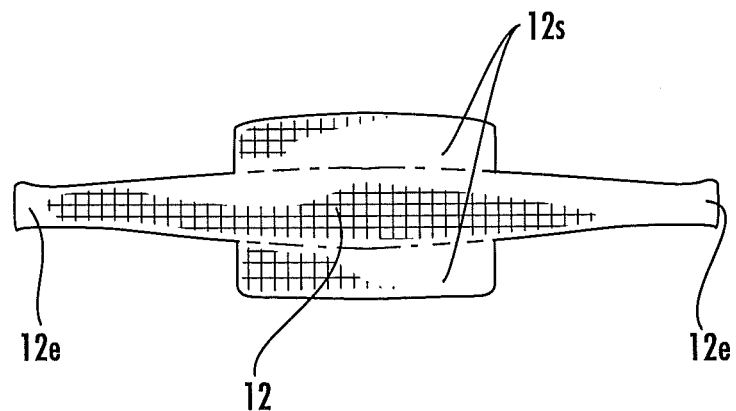
FIG. 2B is a top view of an annular mesh layer that can be used to form the implant shown in FIG. 1A according to embodiments of the invention.

FIGS. 2A and 2B illustrate exemplary configurations of the different mesh pieces 11, 12, 13. FIG. 2B illustrates the peripheral (annulus) mesh ring 12 and FIG. 2A illustrates examples the top and bottom end plate mesh pieces 11, 13. The top and bottom end plate pieces 11, 13 are typically the same or substantially similar, the endplate geometry may vary slightly due to different convexivity of the endplates. As shown, the ends 12e of the peripheral mesh ring can be detached until molded to the implant body as an outer ring. However, in an alternative design, the peripheral mesh ring is a continuous tube or ring member. The ring with the molded polymer body 10b can limit radial expansion of the body 10b in situ. The flexibility of the molded body 10b and integrally attached peripheral mesh ring 12 may allow some limited radial expansion.

As shown in FIGS. 1A, 1B, 2A and 2B, the implant 10 can use a continuation or extension of each of the three pieces of mesh material 11s, 12s, 13s to form a skirt 14 (which can also be described as a tab) reinforced with the molded material, to provide a means for attaching to vertebral bodies. In particular embodiments, the skirt 14 can be between about 1-4 mm thick, typically about 2 mm thick. For the latter, each of the mesh layers can be about 0.75 mm thick. The additional thickness of the skirt 14 is due to the mold material that covers and embeds the layers forming the skirt material 14. None of the mesh layers are required to extend over edges or corners and the mesh is not required to encapsulate the molded body.

The endplate mesh layers 11, 13 may restrain the expansion of the body 10b to some extent in the radial direction, but typically not in the axial direction. The peripheral mesh ring 12 may slightly restrain the primary molded body 10b (e.g., PVA core) in the axial direction due to hydration and the peripheral mesh ring will also limit radial expansion as discussed above. The implant 10 may have certain swelling properties and may be able to expand in all directions between about 1-5% between demolding and full hydration and while unloaded. Also, the implant 10 can be configured to regain height by rehydration when unloaded after height loss due to compressive force. The device 10 may not gain height in situ if unloaded if it does not lose height in the first place.

One primary purpose of the peripheral mesh ring 12 can be to increase radial strength to limit radial expansion under load. The mesh ring 12 may be embedded in the molded material to a sufficient degree so that it does not promote or have significant tissue in-growth. In addition, the tissue in-growth is inhibited if the mesh is not exposed or if the pore size is too small. For example, an exposed peripheral mesh layer having a very small pore size may not experience in-growth.

As noted above, one primary purpose of the mesh on the endplates 11, 13 can be to promote attachment of the device's endplate to the vertebral bodies, primarily by tissue in-growth. To that end, the mesh on at least one of the endplates 11, 13 can be processed before, during and/or after molding to locally expose mesh that otherwise would be or is covered with molded material (e.g., hydrogel) in order to promote the tissue in-growth. The exposure can be carried out so that the mesh is configured to allow for double integration of mesh for fixation of orthopaedic devices: on the one hand, fixation with the device's main material (in some embodiments, hydrogel) and on the other hand, fixation with human tissues (fibrous and/or bone, depending on location and use of the implanted device).

FIG. 4A illustrates that at least one "temporary" removable, solvable and/or resorbable material 20 can be placed over or under the mesh 10m before the mesh 10m is moldably attached to the implant body 10b (while the moldable material is viscous). Where the temporary material 20 is to be implanted, it may comprise a bone substitute. If it is removed prior to implantation it may comprise any suitable material such as any kind of salt, including, for example, calcium salt.

FIG. 4B illustrates the mesh 10m being moldably attached to the body 10b with the removable, solvable or resorbable material remains substantially in position in/on the mesh 10m. FIG. 4C illustrates that the material 20 can be removed to show the locally exposed regions 10e of the mesh 10m. In some embodiments, the material 20 can be peelably removed as shown in FIG. 4C. The material can be a temporary "shield-like" material that is substantially non-porous or less porous than the mesh 10m. For example, the material 20 can be an elastomeric or metal material (or combinations of same, such as an elastomeric sheet or layer with metallic foil backing), such as an impermeable heat-resistant film or conformable flexible metal, either of which may be configured as a single larger piece with apertures or smaller pieces, or other polymer layer configurations, e.g., dollops of silicone, one or more pieces of a second, denser mesh layer, and the like.

In some embodiments, the material 20 can include a material that is solubilized or resorbed to form the locally exposed region(s) 10e. For example, the material 20 can include calcium salt, hydroxyapatite, calcium phosphates and/or any other resorbable and/or solubilizable material to temporarily fill a target volume/area of mesh 10m to expose (e.g., inhibit mold material from integrating thereat). Different materials 20 with different resorbtion rates may be used, typically taking between 3 weeks to several years to substantially resorb after implantation.

The exposed region 10e can extend over substantially an entire or whole primary surface, through partial thickness of the mesh 10m, or the exposed region 10e can be local—one or several sub-portions of segments. For the latter, the exposure can be through a partial thickness for each or some local regions 10e, or throughout the whole thickness of the mesh at that region(s), which may provide improved tissue bonding.

In some embodiments, the material 20 can comprise a viscous liquid such as silicone that can be injected, poured or otherwise provided on the primary surface of the mesh 10m, then cured or otherwise treated to solidify the material.

After the molding process, which integrates the mesh 10m to the implant body 10b, the temporary material 20 can be chemically, electrically, optically or mechanically removed. For example, the temporary material 20 can also be removed during manufacturing using solvent and/or mechanical removal, such as, but not limited to, vibration, peeling of material, brushing of the material, evacuation of the material and the like. In some embodiments, where a viscous liquid is used, the viscous liquid can be solidified, then peeled-off of the surface of the mesh 10m to provide the region(s) 10e. With viscous liquids such as silicone, it is contemplated that the size of the mesh pores to be exposed can be generally or substantially controlled by selecting an appropriate viscosity or durometer, whereby a lower viscosity or durometer can occupy larger areas and/or fill smaller pores to migrate further (deeper) into the mesh layer 10m.

In some embodiments, the material 20 can be a "mesh peel layer" where a section of mesh, impregnated with CaS or other anti-stick material suitable to facilitate removal after exposure to the molding process, can be placed on and/or a depth into the uppermost (or lowermost) primary surface of the target mesh 10m (i.e., inferior and superior endplates 11, 13) through the molding process, then peeled, pulled or scraped off at demolding.

In some embodiments, all or some of the material 20 remains in place at implantation, and, if bio-resorbable, the tissue ingrowth can occur while the material 20 is resorbed (e.g., calcium salt). This technique may inhibit collapse of the exposed mesh scaffold 10e under compressive loads.

FIG. 5 illustrates that an insert material 30 can be placed between the mesh 10m and the primary implant molded body 10b. The insert material 30 may be used alone (FIG. 6A) or with the temporary outer material 20 (FIG. 5). The insert material 30 can be configured to locally inhibit the moldable material (e.g., hydrogel material) from flowing out through the mesh 10m during molding. The flowing of the moldable material through the mesh 10m typically allows the mold material to enter and embed the mesh 10m to attach the mesh to the implant body 10b. As shown in FIG. 6B, by locally inhibiting this interaction during molding, the material 30 can provide an exposed region 10e at the point of demolding of the formed device, without requiring additional processing. The insert material 30 can be configured as small insert sections 30s of high density/low porosity mesh which can be located adjacent to and right underneath the mesh 10m (e.g., the endplate mesh layers 11, 12). Those allow the irrigation fluid (e.g., saline) but not the liquid (molten) mold material (e.g., hydrogel) to flow through. Alternatively, or additionally, small sections of film 30s (substantially impermeable/or without porosity) can be used as the inner material 30. The film can comprise an elastomer, such as a polymer, copolymer or derivatives thereof, such as silicone, TEDLAR and other suitable heat-resistant materials. Again, during molding, the irrigant (e.g., saline) can flow around the insert, but not the moldable material (e.g., hydrogel) that forms the primary body 10b and integrates into the other portions of the mesh 10m. At demolding, the saline in the non-integrated mesh regions flows out/dehydrated, leaving an exposed area 10e of mesh.

Where small pieces of insert material 30 are used, the small sections may have an area of between about 1 mm$^2$ to about 25 mm$^2$. The inserts 30 can be provided as combinations of different material types, such as pieces of mesh and film.

Alternatively, as shown in FIG. 6C, the film, mesh or other insert material 30 can be configured as a single layer with a pattern of apertures 30p to allow sufficient transfer of irrigant to permit at least a major portion of the mesh 10m to moldably affix to the implant body 10b while also providing exposed mesh 10e. A similar shield temporary layer 20 may also be used in lieu of smaller droplets, globules or pieces of material 20.

FIGS. 7A-7C illustrate different exposed mesh regions 10e that can be formed using removable material 20 according to embodiments of the present invention. The mesh 10m (e.g., mesh scaffold) is moldably attached to the primary implant body 10b typically formed of a solid freeze-thaw crystalline hydrogel. The moldable material 100 is configured to flow through the mesh during the molding process to integrate into the mesh 10m. The removable material 20 is configured to expose certain portions of the mesh to allow tissue in-growth. FIG. 7A illustrates that the material 20 can be configured to cover a relatively large region of the mesh 10m from a first primary surface to a partial depth or thickness $t_p$. FIG. 7B illustrates that the material 20 can be configured to reside locally at a relatively small segment of the mesh and extend through the mesh 10m substantially to a total or whole thickness, $t_w$. FIG. 7C illustrates that the material 20 can extend to several depths or thickness, including partial (which extends over a greater surface area), and through the mesh entirely to a depth of $t_t$ to contact an upper (or lower) portion of the molded body 10b. The removable material 20 can be removed to define the locally exposed regions 10e of the mesh 10m.

Figure 8:
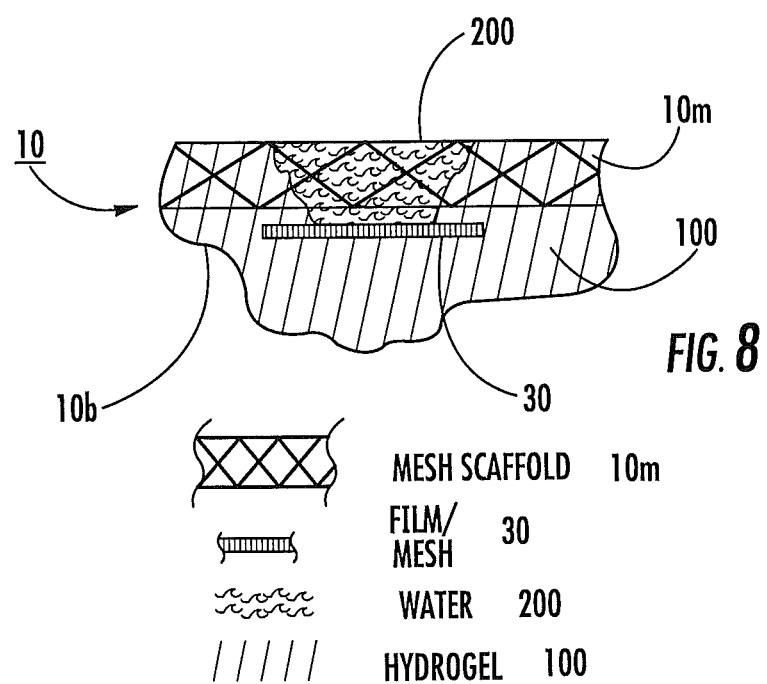
FIG. 8 is a schematic illustration of an implant with an inner layer according to embodiments of the invention.

FIG. 8 illustrates an exemplary use of the insert material 30. As shown, the insert member 30 resides under the mesh 10m (mesh scaffold) adjacent a top portion of the molded implant body 10b. During processing, the moldable material 100 may flow over the edges of the protective insert material 30. Typically, a gradient of moldable material will be formed between the liquid irrigant (water or saline) volume 200 and the moldable material volume (forming the primary implant body 10b), lesser to greater. The liquid 200 can be removed after processing to provide the exposed mesh 10e.

Figure 9A:
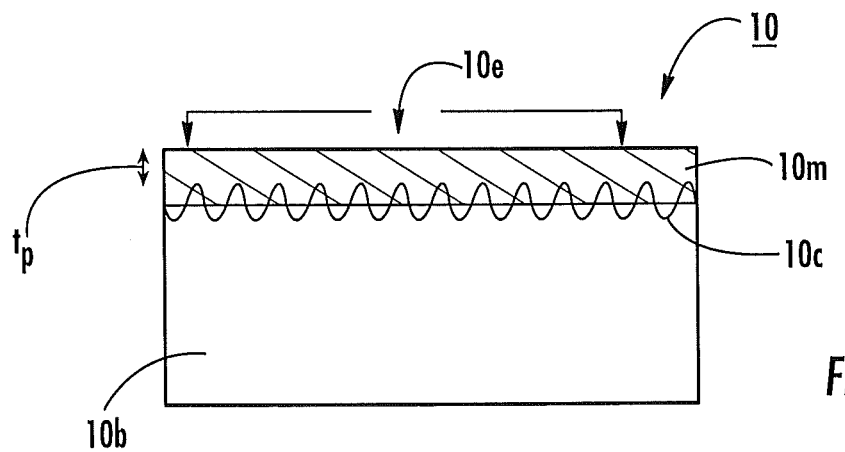
FIG. 9A is a schematic illustration of an implant with the mesh layer having opposing upper and lower primary surfaces, at least a major portion of the lower surface being integrally attached to the molded body such that the moldable material extends through a partial thickness of the mesh substrate leaving an upper portion of the mesh substantially devoid of the molded material to facilitate tissue in-growth.
Figure 9B:
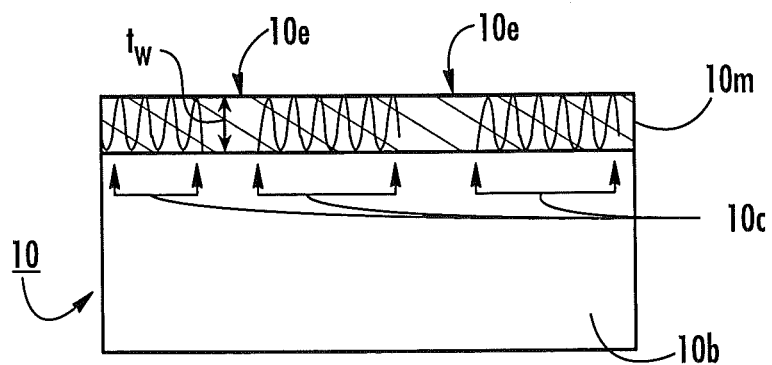
FIG. 9B is a schematic illustration of an implant with the mesh layer having opposing upper and lower primary surfaces, at least a major portion of the lower surface being integrally attached to the molded body such that the exposed mesh extends through the mesh substrate to facilitate tissue in-growth.

FIG. 9A illustrates an implant 10 with an integrated mesh 10m such that at least a major portion of the contact surface 10c of the mesh 10m is moldably attached to the implant body 10b and the mesh 10m has at least one locally exposed region 10e that extends a partial depth thickness $t_p$ of the mesh 10m. The region 10e may be relatively large and contiguous or discontinuous and may occupy between about 20-70% of the upper surface and extend to a partial depth over most of that region, with potentially deeper depth extension in sub-regions. As shown in FIG. 9B, where smaller localized regions 10e are used, the regions 10e may extend partially, but typically at least some regions 10e extend through or to a total mesh depth $t_w$. Where a keel 15 (FIG. 1A) is used, the regions 10e can be configured to accommodate this feature.

Figure 10:
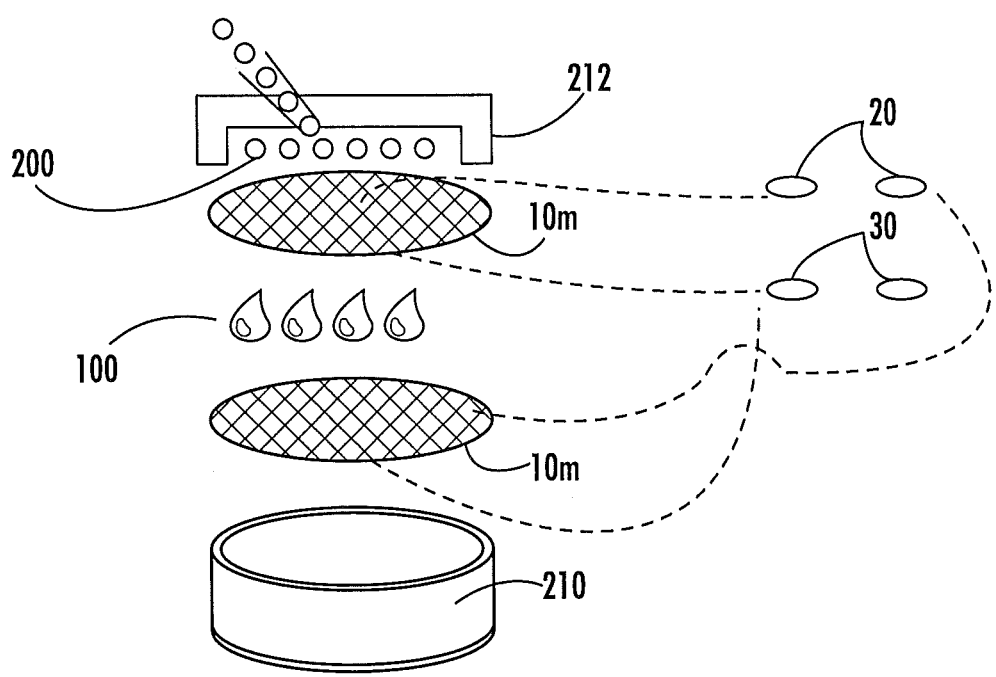
FIG. 10 is an exploded view of a mold with components used to make a molded primary implant body with a mesh scaffold and a removable outer layer and/or an integrated internal shielding layer according to embodiments of the invention.

FIG. 10 is an exploded view of a mold 210 with components used to make a molded primary implant body 10b with two mesh scaffolds 10m and a removable outer material 20 and/or an integrated internal insert material 30 used to form the exposed region(s) according to embodiments of the invention. As shown the lower mesh 10m can be placed in the mold 210 and the moldable material can be placed over the lower mesh 10m. The upper mesh 10m can be placed on top of the moldable material 200. Liquid irrigant 200 can be added before and/or after the lid 212 is placed on the mold 210. The lid 210 can have a channel or port to add liquid 200. The insert material 30 and/or the removable material 20 can be placed in the order needed to have them in the mold and in communication with the respective mesh 10m at the appropriate time. That is, for the insert 30, the insert material can be placed after the lower mesh 10m is placed in the mold 210, before the moldable material 100 is added. In contrast, where a removable material 20 is used, the material 20 can be placed on the lower part (outer surface) of the mesh 10m and/or in the bottom of the mold prior to placing the mesh in the mold. For the top mesh 10m, where an insert material 30 is used, the material 30 can be placed on the moldable material 100 or on the underside of the mesh 10m before the mesh is added to the mold 210. For the removable material 20, the material can be added to the mesh 10m before, during or after the mesh 10m is placed in the mold. The lid 212 can enclose the components therein and the mold can be placed at the desired temperature to mold the body and attach the mesh thereto. The exposed regions 10e may exist at demolding, or may be exposed after additional processing.

Alternatively, the exposed regions 10e can be formed after demolding without the use of either material 20 or 30, using chemical, optical, mechanical or electrical formation means. Combinations of any of the above may also be used.

Figure 16:
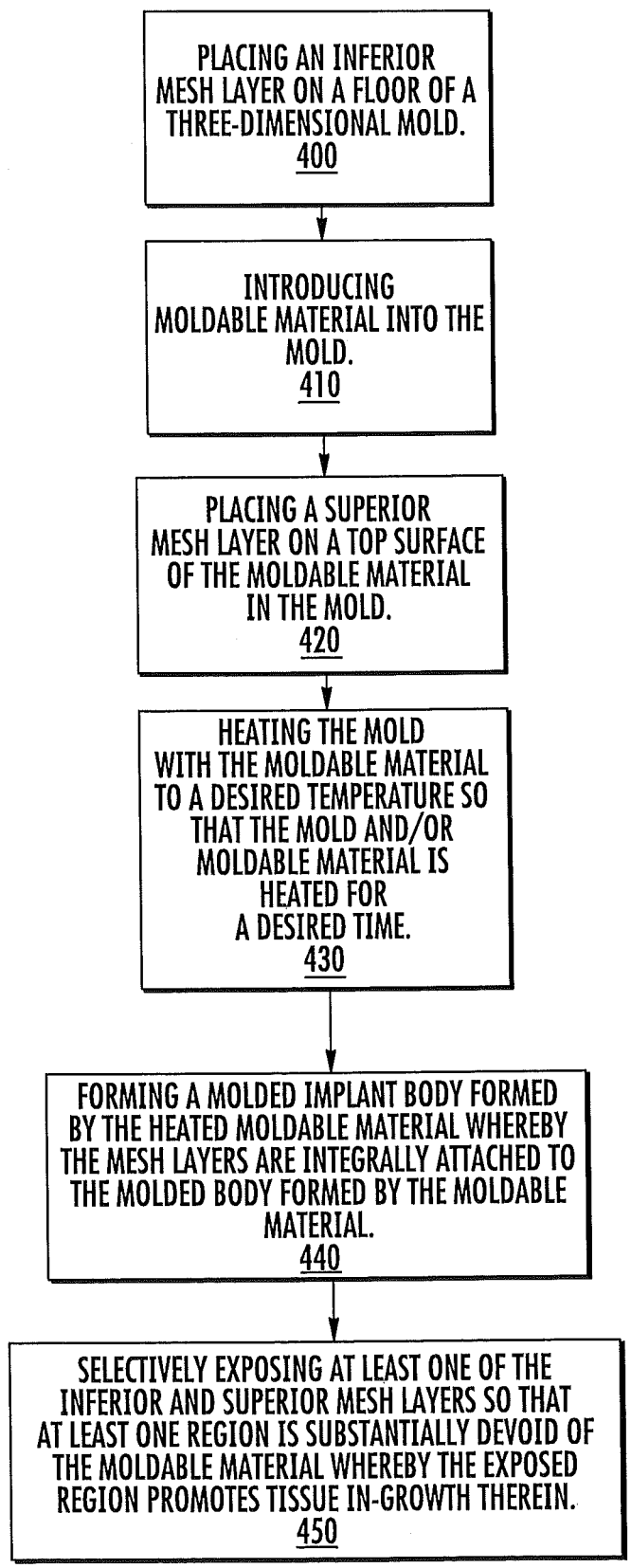
FIG. 16 is a flow chart of operations that can be used to fabricate surgical implants according to embodiments of the present invention.

FIG. 16 illustrates exemplary operations that can be used to form at least one exposed mesh region in a molded implant with inferior and superior mesh layers. As shown, an inferior mesh layer can be placed on a floor of a three-dimensional mold (block 400). Moldable material can be introduced into the mold (block 410). A superior mesh layer can be placed over the moldable material (block 420). The mold with the moldable material and mesh can be heated (block 430). The molded implant body is formed by the heated molded material whereby the mesh layers are integrally molded to the implant body formed by the molded material (block 440). At least one of the inferior and superior mesh layers is selectively exposed so that at least one region thereof is devoid of moldable material whereby the exposed region allows for tissue in-growth in situ (block 450).

Figure 11A:
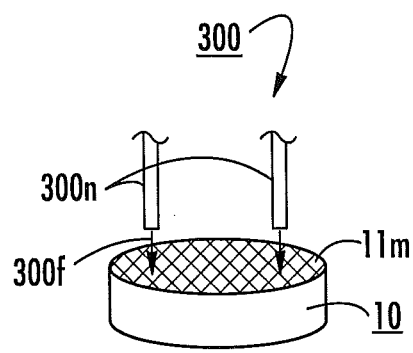
FIG. 11A is a schematic illustration of a pressurized fluid material removal system configured to remove local regions of molded (hydrogel) material from the mesh according to embodiments of the invention.

As shown in FIG. 11A, a fluid removal system 300 using pressurized fluid 300f delivered via one or more flow jets or nozzles 300n can be used to form locally exposed regions 10e in the mesh 10m. No special preparation is required to form the exposed mesh before molding. Rather, after demolding, the molded material (e.g., hydrogel) can be "pressure-washed" or removed from the desired local area/volume of mesh using a pressurized fluid, typically a heated sterile liquid at a temperature between about 70° C.-95° C., such as heated sterile water or saline.

In some embodiments, a focal water jet (pressurized to between about 50 psi to about 150 psi) can be pulsed at a desired frequency, typically below about 100 Hz, such as at about 50 Hz to about 5 Hz, typically about 20 Hz, to improve removal of the molded material 100. This process can be carried out to remove material in depth (throughout the layer of mesh and even below).

Figure 11B:
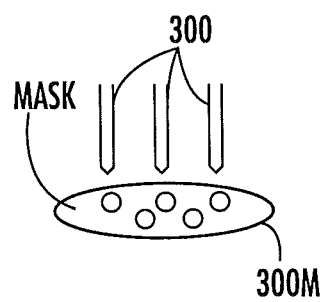
FIG. 11B is a schematic illustration of pressurized fluid system shown in FIG. 11A, with a template used to direct the fluid to target locations and/or shield non-target locations according to embodiments of the invention.

FIG. 11B illustrates a mask 300m with apertures can be used to help direct the fluid to form the desired exposed regions 10e and/or help shield non-target mesh regions. The fluid may be a sterile liquid, such as heated saline or water.

Figure 12:
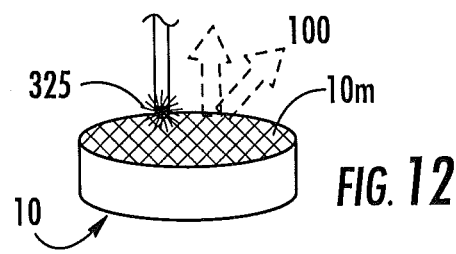
FIG. 12 is a schematic illustration of a mechanical material removal system according to embodiments of the invention.

FIG. 12 illustrates that a stiff brush 325, such as a wire brush, can be used to contact the molded body and mesh 10m to remove molded material 100 to expose local regions of mesh. The brush 325 or other mechanical device can be used with moisture (solvent) and/or heat to facilitate the removal.

Figure 13:
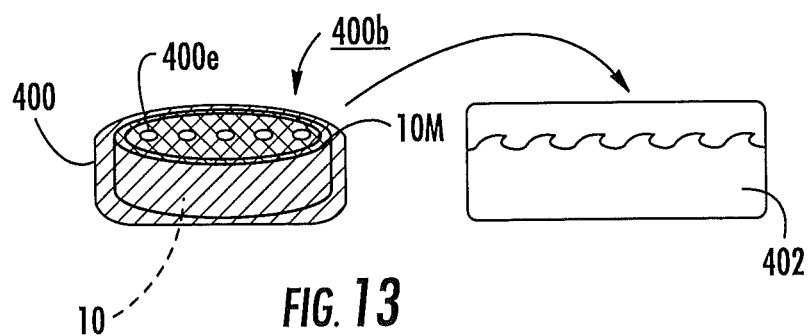
FIG. 13 is a schematic illustration of a substantially encapsulating shield cooperating with a solvent removal system according to embodiments of the present invention.

FIG. 13 illustrates that the molded implant 10 with integrated mesh 10m can be substantially encapsulated in a shield 400 with locally exposed regions 400e. This encapsulated body 400b can open only the target area(s) to expose those areas where the molded material is desired to be removed. The encapsulated body 400b can then be immersed in a bath 402 of solvent, which would substantially contact only the area(s) to expose. The bath 402 can comprise heated liquid, such as sterile (sub)boiling water. The bath 402 may be stationary or may vibrate and/or oscillate similar to a dishwasher. This method emphasizes the non-directional use of the solvent.

Figure 14:
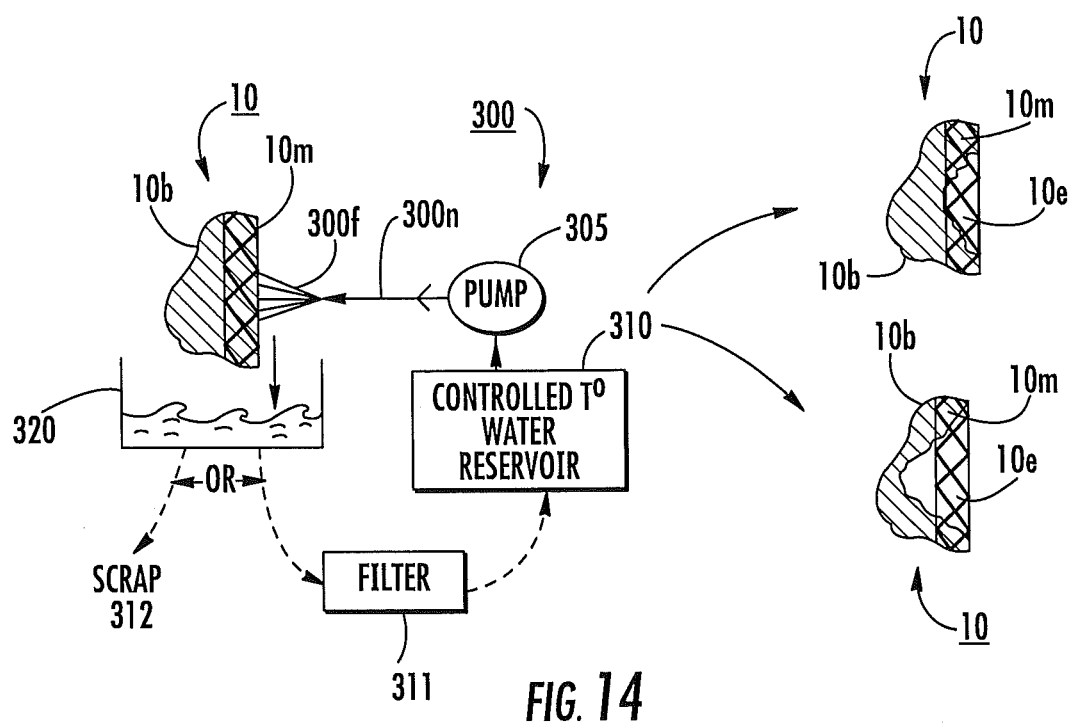
FIG. 14 is a schematic illustration of a pressurized material removal system with different exemplary exposed mesh configurations according to embodiments of the present invention.

FIG. 14 illustrates another fluid removal system 300. In this embodiment, the system 300 includes a controlled-temperature liquid reservoir 310, a pump 305, a nozzle 300n and an overflow or liquid capture container 320. If the used liquid is re-used in a re-circulating contained circuit, a filter 311 can be placed between the reservoir 310 and the container 320. If the waste or used liquid is disposed, then the filter may not be required. The pressurized fluid 300f employed in the contained circuit to remove the material 100 can be pressurized hot water. The system 300 can form exposed regions 10e with either partially, totally or even deeper exposure regions as shown by the exemplary exposed region 10e configurations to the right of the system 300 in FIG. 14.

Figure 15:
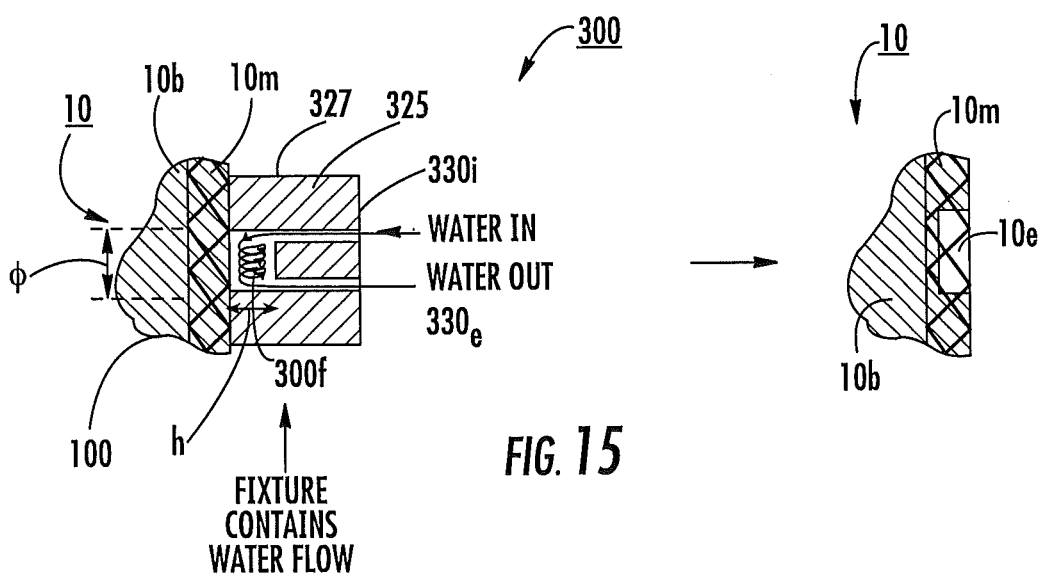
FIG. 15 is a schematic illustration of a contacting pressurized removal system with an exemplary exposed mesh configuration according to embodiments of the invention.

FIG. 15 illustrates a fluid removal system 300 with a fixture 325 with a chamber 327 that is in communication with inlet and exit flow paths 330i, 330e and abuts a primary surface of the mesh 10m. The controlled temperature reservoir 310 can connect to the chamber 327 with a pipe diameter of about 2 mm. The chamber 327 can have about a 5 mm diameter (or width) and about a 5 mm height ("h") (corresponding to the area or diameter of the target region to expose) with between about a 90 degree to about a 180 degree angle between the input 330i and output 330e. The diameter change and angles create a pressure drop and a turbulent flow around the molded material 100 (e.g., hydrogel) to facilitate material removal. The chamber-based system and/or method provides control of depth of exposed region of mesh as the solvent flows substantially tangentially to the mesh, which eventually dampens/shields the internal core material (e.g., the primary implant body 10b). Thus, FIGS. 14 and 15 illustrate that in some embodiments, the selectively exposing step comprises directing liquid, which may be pressurized to higher or lower pressures, or even unpressurized (just flowing), to remove molded material residing in a target, localized region of at least one of the superior and inferior mesh layers.

For each of the fluid removal systems, the pump 305 used can be any suitable pump, such as, but not limited to, a peristaltic pump, and may provide a typical flow rate of between about 250-1000 mL/min.

As noted above, a chemical removal/breakdown of the molded material 100 (e.g., hydrogel) can also or alternatively be used to remove the molded material from a desired area/volume of mesh 10m. Also, any combination or two or more of the above methods can be used. For example, using the insert 30 or shield layer 20 to selectively expose the mesh during molding, then washing such as using the pressurized fluid may remove any residual mold material such as, for example, low weight % hydrogel.

In some embodiments, the shape of the implant 10 can be described as a three-dimensional structure that provides anatomical shape, shock absorbency and mechanical support. The anatomical shape can have an irregular solid volume to fill the target intervertebral disc space. The coordinates of the body can be described using the anatomic directions of superior (towards the head), inferior (towards the feet), lateral (towards the side), medial (towards the midline), posterior (towards the back), and anterior (towards the front). From a superior view, the implanted device has a kidney shape with the hilum towards the posterior direction. The margins of the device in sagittal section are generally contained within the vertebral column dimensions. The term "primary surface" refers to one of the superior or inferior surfaces.

The molded implant 10 can be made from any suitable elastomer capable of providing the desired shape, elasticity, bio compatibility, and strength parameters. The implant 10 can be configured with a single, uniform average durometer material and/or may have non-linear elasticity (i.e., it is not constant). The implant 10 may optionally be configured with a plurality of durometers, such as a dual durometer implant. The implant 10 can be configured to be stiffer in the middle, or stiffer on the outside perimeter. In some embodiments, the implant 10 can be configured to have a continuous stiffness change, instead of two distinct durometers. A lower durometer corresponds to a lower stiffness than the higher durometer area. For example, one region may have a compressive modulus that is between about 11-100 MPa while the other region may have a compressive modulus that is between 1-10 MPa.

The implant 10 can have a tangent modulus of elasticity that is about 1-10 MPa, typically about 3-5 MPa, and water content of between about 30-60%, typically about 50%.

Some embodiments of the implantable spinal disc 10 can comprise polyurethane, silicone, hydrogels, collagens, hyalurons, proteins and other synthetic polymers that are configured to have a desired range of elastomeric mechanical properties, such as a suitable compressive elastic stiffness and/or elastic modulus. Polymers such as silicone and polyurethane are generally known to have (compressive strength) elastic modulus values of less than 100 MPa. Hydrogels and collagens can also be made with compressive elasticity values less than 20 MPa and greater than 1.0 MPa. Silicone, polyurethane and some cryogels typically have ultimate tensile strength greater than 100 or 200 kiloPascals. Materials of this type can typically withstand torsions greater than 0.01 N-m without failing.

Although shown as substantially conformally covering substantially the entire respective surfaces of the implant, one or more of the layers 11, 12, and 13 may occupy a smaller portion of the respective surface (not shown).

Some embodiments of the spinal disc implant 10 are configured so that they can mechanically function as a substantially normal (natural) spinal disc and can attach to endplates of the adjacent vertebral bodies. The implant 10 can expand in situ to restore the normal height of the intervertebral space. The implant 10 can be configured to expand, for example, between about 1-40%, typically about 1-5%, after implantation relative to its configuration at the time of implantation. It is envisioned that the spinal disc implant 10 can be inserted by a surgical procedure into the target intervertebral space. It may be used for separation of two bony surfaces within the spine. In other embodiments, the implant may be configured for use with respect to other bones of the body.

As shown in FIG. 1A, the spinal disc body 10 is generally of kidney shape when observed from the superior, or top, view, having an extended oval surface and an indented portion. The implant 10 can be configured with a mechanical compressive modulus of elasticity of about 1.0 MPa, ultimate stretch of greater than 15%, and ultimate strength of about 5 MPa. The device can support over 1200 N of force. Further description of an exemplary flexible implant is described in co-pending U.S. Patent Application Publication No. 20050055099, the contents of which are hereby incorporated by reference as if recited in full herein.

Elastomers useful in the practice of the invention include silicone rubber, polyurethane, polyvinyl alcohol (PVA) hydrogels, polyvinyl pyrrolidone, poly HEMA, HYPAN™ and Salubria® biomaterial. Methods for preparation of these polymers and copolymers are well known to the art. Examples of known processes for fabricating elastomeric cryogel material are described in U.S. Pat. Nos. 5,981,826 and 6,231,605, and co-pending, co-assigned U.S. Patent Application Ser. No. 60/60/761,902, the contents of which are hereby incorporated by reference. See also, Peppas, Poly (vinyl alcohol) hydrogels prepared by freezing—thawing cyclic processing. Polymer, v. 33, pp. 3932-3936 (1992); Shauna R. Stauffer and Nikolaos A. Peppas.

The moldable material comprises an irrigant and/or solvent and can comprise between about 25 to 60% (by weight) PVA powder crystals. The PVA powder crystals can have a MW of between about 124,000 to about 165,000, with about a 99.3-100% hydrolysis. The irrigant or solvent can be a solution of about 0.9% sodium chloride. The PVA crystals can be placed in the mold 210 (FIG. 10) before the irrigant (no pre-mixing is required). The lid 212 can be used to close the mold 210. The closed mold 200 can be evacuated or otherwise processed to remove air bubbles from the interior cavity. For example, the irrigant can be overfilled such that when the lid is placed on (clamped or secured to) the mold 210; the excess liquid is forced out thereby removing air bubbles. In other embodiments, a vacuum can be in fluid communication with the mold cavity to lower the pressure in the chamber and remove the air bubbles. The PVA crystals and irrigant can be mixed once in the mold or before and placed in the mold together and/or some or all of the irrigant can be introduced after the lid is closed. Alternatively, the mixing can occur naturally without active mechanical action during the heating process. The irrigant or solvent can comprise saline which may be provided as a solution of about 0.9% sodium chloride. The PVA crystals can be placed (dry) in the mold independently of, typically before, the irrigant (no pre-mixing is required) and/or otherwise introduced into the mold so that injection is not required. The irrigant and PVA, or just the irrigant, can be inserted into a mold after a lid is attached using a liquid vent port that can be plugged or sealed before the material and the mold are heated. After cooling, the hydrogel-molded body can be further processed without placing in water or saline during subsequent processing. The hydrogel body can be hydrated at least partially before packaging and/or before implantation.

Typically, for PVA mold material, the mold 210 with the moldable material is heated to a temperature of between about 80° C. to about 200° C. for a time sufficient to form a solid molded body. The temperature of the mold can be measured on an external surface. The mold can be heated to at least about 80-200° C. for at least about 5 minutes and less than about 8 hours, typically between about 10 minutes to about 4 hours, the (average or max and min) temperature can be measured in several external mold locations. The mold can also be placed in an oven and held in the oven for a desired time at a temperature sufficient to bring the mold and the moldable material to suitable temperatures. In some embodiments, the mold(s) can be held in an oven at about 100-200° C. for about 2-6 hours. The higher range may be used when several molds are placed therein, but different times and temperatures may be used depending on the heat source, such as the oven, the oven temperature, the configuration of the mold, and the number of items being heated.

For PVA mold material, after heating, the implant body 10b can be cooled passively or actively and/or frozen and thawed a plurality of times until a solid crystalline implant is formed with the desired mechanical properties. The molded implant body can be removed from the mold prior to the freezing and thawing or the freezing and thawing can be carried out with the implant in the mold. Alternatively, some of the freeze and thaw steps (such as, but not limited to, between about 0-10 cycles) can be carried out while the implant is in the mold, then others (such as, but not limited to, between about 5-20 cycles) can be carried out with the implant out of the mold.

Before, during and/or after freezing and thawing (but typically after demolding), the molded implant 10 can be placed in water or saline (or both or, in some embodiments, neither). The device 10 can be partially or completely dehydrated for implantation. The resulting prosthesis can have an elastic modulus of at least about 2 MPa and a mechanical ultimate strength in tension and compression of at least 1 MPa, preferably about 10 MPa, and under about 100 MPa. The prosthesis may allow for between about 1-10 degrees of rotation between the top and bottom faces with torsions of at least about 1 N-m without failing. The implant can be a single solid elastomeric material that is biocompatible by cytotoxicity and sensitivity testing specified by ISO (ISO 10993-5 1999: Biological evaluation of medical devices—Part 5: Tests for in vitro cytotoxicity and ISO 10993-10 2002: Biological Evaluation of medical devices—Part 10: Tests for irritation and delayed-type hypersensitivity).

The testing parameters used to evaluate the compressive tangential modulus of a material specimen can include:
Test type: unconfined compression
Fixtures: flat platens, at least 30 mm diameter
Rate: 25.4 mm/sec to 40% strain
Temperature: room temp (~22° C.)
Bath: samples stored in saline or water until immediately before test
Samples: cylinders, 9.8±0.1 mm height, 9.05±0.03 mm diameter
Compressive Tangential Modulus Calculated at 15, 20, and 35% Strain Because the implants can be manufactured to be mechanically strong, or to possess various levels of strength among other physical properties, the process can be adapted for use in many applications. Cryogel-based mold material also has a high water content, which provides desirable properties in numerous applications. For example, the cryogel tissue replacement construct is especially useful in surgical and other medical applications as an artificial material for orthopedic implants in humans and other mammals.

Orthopaedic implants include, but are not limited to, back, knee, arm implants, hip and knee joint replacements, load bearing surface implants and prosthetic limbs.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of fabricating an implantable prosthesis, comprising:
    placing an inferior mesh layer on a floor of a three-dimensional mold;
    introducing moldable material into the mold;
    placing a superior mesh layer on a top surface of the moldable material in the mold;
    heating the mold with the moldable material to a desired temperature so that the mold is heated for a desired time; then
    forming a molded implant body formed by the heated moldable material whereby the mesh layers are integrally moldably attached to inferior and superior surfaces of the molded body formed by the moldable material; and
    selectively exposing at least one of the inferior and superior mesh layers so that at least one region is substantially devoid of the moldable material whereby the exposed region promotes tissue in-growth therein while at least a major portion of the mesh layers are integrally moldably attached to the molded body.

2. A method according to claim 1, wherein the selectively exposing step comprises placing a temporary mesh layer over at least a portion of at least one of an upper primary surface of the superior mesh layer or a lower primary surface of the inferior mesh layer, then after the forming step, removing the temporary mesh layer to selectively expose the mesh of the superior and/or inferior mesh layers.

3. A method according to claim 1, wherein the selectively exposing step comprises placing a resorbable material on selective regions of the inferior and superior mesh layers before the forming step.

4. A method according to claim 1, wherein the selectively exposing step comprises placing a temporary silicone layer over at least a portion of at least one of an upper primary surface of the superior layer or a lower primary surface of the inferior mesh layer to inhibit moldable material from entering at least a top portion of the superior mesh layer or a bottom portion of the inferior mesh layer, respectively, during the forming step, then after the forming step, removing the temporary silicone layer to selectively expose the mesh of the superior and/or inferior mesh layers.

5. A method according to claim 1, wherein the selectively exposing step comprises placing intermediate mesh segment layers having smaller areas than the inferior and superior mesh layers, between at least one of the superior layer or the inferior mesh layer and the moldable material to locally inhibit moldable material from entering selected regions of the superior mesh layer and the inferior mesh layer, respectively.

6. A method according to claim 1, wherein the superior and inferior mesh layers are planar and are attached only to respective upper and lower surfaces of the molded implant body, and wherein the selectively exposing step comprises inhibiting the moldable material from extending through localized regions of an upper portion of the superior mesh layer and a lower portion of the inferior mesh layer during the forming step.

7. A method according to claim 1, wherein the superior and inferior mesh layers are planar and are attached only to respective upper and lower surfaces of the molded implant body, and wherein the selectively exposing step comprises allowing the moldable material to enter the mesh superior and inferior layers while inhibiting the moldable material from extending through at least a major portion of an area of an upper portion of the superior mesh layer and a lower portion of the inferior mesh layer during the forming step.

8. A method according to claim 1, wherein the selectively exposing step comprises placing a temporary mesh layer comprising calcium salt over at least a portion of at least one of an upper primary surface of the superior mesh layer or a lower primary surface of the inferior mesh layer, then after the forming step, removing the temporary mesh layer to selectively expose the mesh of the superior and/or inferior mesh layers.

9. A method according to claim 1, wherein the selectively exposing step comprises directing pressurized liquid to remove material throughout a target localized region in at least one of the superior and inferior mesh layers.

10. A method according to claim 1, wherein the selectively exposing step comprises further comprising at least one of optically, chemically or mechanically removing molded material from at least one upper region of the superior mesh layer and at least one lower region of the inferior mesh layer after the forming step.

11. A method according to claim 1, wherein the selectively exposing step comprises shielding the molded implant body with the attached inferior and superior mesh layers while exposing at least one target exposure area, then immersing the shielded implant body with the at least one target exposure area in a solvent bath.

12. A method according to claim 1, wherein the forming step forms a total disc replacement spinal disc.

13. A method according to claim 1, wherein the superior and inferior mesh layers comprise a polyester mesh material having a thickness that is between about 5 mm to about 0.5 mm.

14. A method according to claim 1, wherein the mesh layers are planar and moldably attached to respective superior and inferior surfaces of the molded body.

15. A method according to claim 14, wherein the molded body comprises solid PVA hydrogel.

16. A method of fabricating an implantable prosthesis, comprising:
    placing an inferior mesh layer on a floor of a three-dimensional mold;
    introducing moldable material into the mold;
    placing a superior mesh layer on a top surface of the moldable material in the mold;
    heating the mold with the moldable material to a desired temperature so that the mold is heated for a desired time; then forming a molded implant body formed by the heated moldable material whereby the mesh layers are integrally moldably attached to the molded body formed by the moldable material; and selectively exposing at least one of the inferior and superior mesh layers so that at least one region is substantially devoid of the moldable material whereby the exposed region promotes tissue in-growth therein while at least a major portion of the mesh layers are integrally moldably attached to the molded body, wherein the selectively exposing step comprises placing an intermediate substantially impermeable layer between at least one of the superior layer or the inferior mesh layer and the moldable material to locally inhibit moldable material from entering selected regions of the superior mesh layer or the inferior mesh layer, respectively, during the forming step.

17. A method of fabricating an implantable prosthesis, comprising:

placing an inferior mesh layer on a floor of a three-dimensional mold;

introducing moldable material into the mold;

placing a superior mesh layer on a top surface of the moldable material in the mold;

heating the mold with the moldable material to a desired temperature so that the mold is heated for a desired time; then forming a molded implant body formed by the heated moldable material whereby the mesh layers are integrally moldably attached to the molded body formed by the moldable material; and selectively exposing at least one of the inferior and superior mesh layers so that at least one region is substantially devoid of the moldable material whereby the exposed region promotes tissue in-growth therein while at least a major portion of the mesh layers are integrally moldably attached to the molded body, wherein the selectively exposing step comprises flowing PVA hydrogel moldable material into the inferior and superior mesh layers during the forming step whereby a density gradient of the hydrogel moldable material extends in the mesh substrate whereby a lesser density of moldable material resides on an outermost bounds of the implant body.

18. A method of fabricating an implantable prosthesis, comprising:

placing an inferior mesh layer on a floor of a three-dimensional mold;

introducing moldable material into the mold;

placing a superior mesh layer on a top surface of the moldable material in the mold;

heating the mold with the moldable material to a desired temperature so that the mold is heated for a desired time; then forming a molded implant body formed by the heated moldable material whereby the mesh layers are integrally moldably attached to the molded body formed by the moldable material; and selectively exposing at least one of the inferior and superior mesh layers so that at least one region is substantially devoid of the moldable material whereby the exposed region promotes tissue in-growth therein while at least a major portion of the mesh layers are integrally moldably attached to the molded body, wherein the selectively exposing step comprises directing pressurized liquid to remove material throughout a target localized region in at least one of the superior and inferior mesh layers, and wherein the pressurized liquid is a jet stream of heated and pulsed sterile water or saline directed to expose a desired local area and/or volume of the superior and/or inferior mesh layers.

19. A method of fabricating an implantable prosthesis, comprising:

placing an inferior mesh layer on a floor of a three-dimensional mold;

introducing moldable material into the mold, wherein the moldable material includes PVA crystals and a liquid irrigation solution that defines a PVA hydrogel;

placing a superior mesh layer on a top surface of the moldable material in the mold;

heating the mold with the moldable material to a desired temperature so that the mold is heated for a desired time, wherein the heating is carried out to heat the mold with the moldable material to between about 80-200° C. for at least about 5 minutes to less than about 8 hours; then forming a molded implant body formed by the heated moldable material whereby the mesh layers are integrally moldably attached to the molded body formed by the moldable material;

closing the mold before the forming step;

selectively exposing at least one of the inferior and superior mesh layers so that at least one region is substantially devoid of the moldable material whereby the exposed region promotes tissue in-growth therein while at least a major portion of the mesh layers are integrally moldably attached to the molded body; and freezing and thawing the PVA hydrogel molded body a plurality of times after the heating to provide a crystalline implant body with a desired compressive modulus of elasticity.

* * * * *

UNITED STATES PATENT AND TRADEMARK OFFICE
CERTIFICATE OF CORRECTION

PATENT NO. : 8,475,503 B2  
APPLICATION NO. : 12/977336  
DATED : July 2, 2013  
INVENTOR(S) : Denoziere et al.

Page 1 of 1

It is certified that error appears in the above-identified patent and that said Letters Patent is hereby corrected as shown below:

On Title Page:
Item 57, Abstract, Line 1: Please correct "molded orthopedic implants"
to read -- molded orthopaedic implants --

Signed and Sealed this
Nineteenth Day of August, 2014

Michelle K. Lee
*Deputy Director of the United States Patent and Trademark Office*